US00PP33583P2

(12) United States Plant Patent
Heuger

(10) Patent No.: US PP33,583 P2
(45) Date of Patent: Oct. 26, 2021

(54) ***HELLEBORUS* PLANT NAMED 'COSEH 7400'**

(50) Latin Name: ***Helleborus niger* X *Helleborus* x *hybridus***
Varietal Denomination: COSEH 7400

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 140 days.

(21) Appl. No.: 16/873,635

(22) Filed: May 27, 2020

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ..... A01H 5/02; A01H 5/00; A01H 6/72
See application file for complete search history.

*Primary Examiner* — June Hwu
(74) *Attorney, Agent, or Firm* — C. Anne Whealy

(57) ABSTRACT

A new and distinct cultivar of *Helleborus* plant named 'COSEH 7400', characterized by its upright to slightly outwardly spreading and mounded plant habit; moderately vigorous growth habit; dark green-colored leaves; moderately freely flowering habit; large light yellow green to white-colored flowers with red purple-colored margins and reverse; and good garden performance.

2 Drawing Sheets

Figure 1:
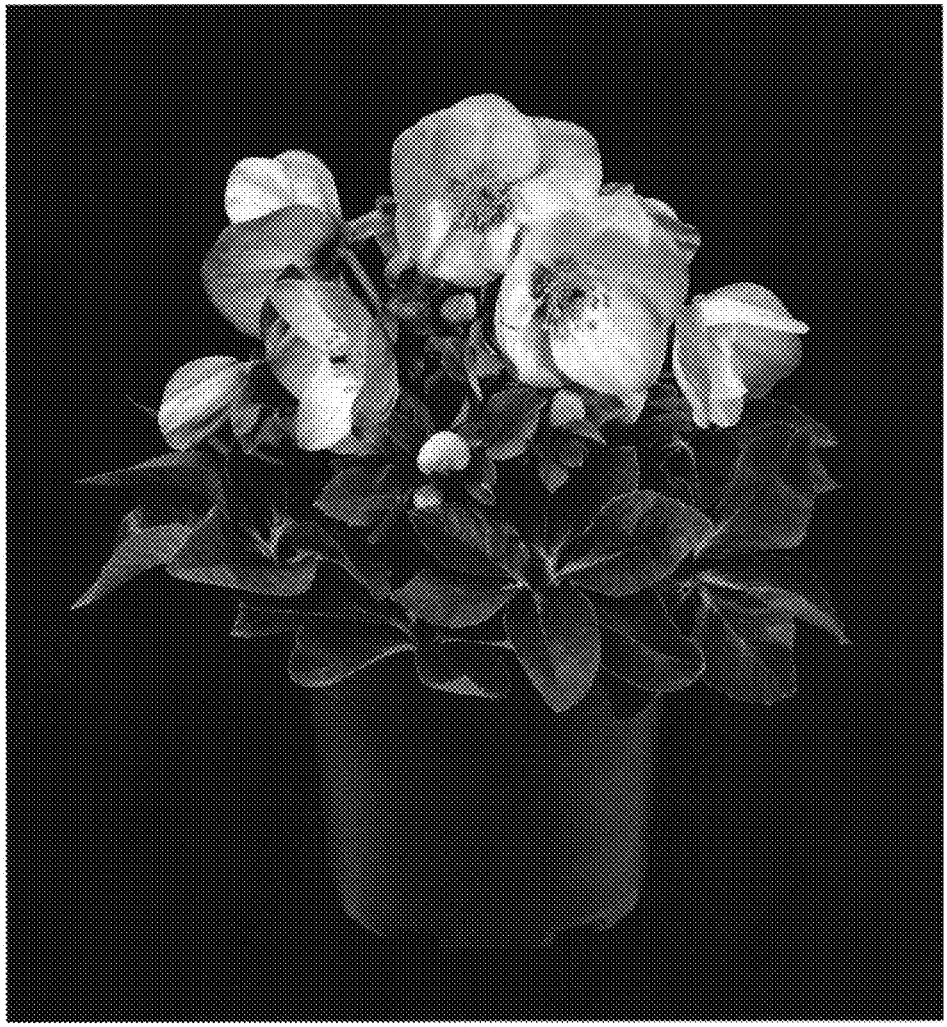

Botanical designation: *Helleborus niger* X *Helleborus* x *hybridus*.
Cultivar denomination: 'COSEH 7400'.

CROSS-REFERENCED TO CLOSELY-RELATED APPLICATIONS

Title: *Helleborus* Plant Named 'COSEH 7300'
Inventor/Applicant: Josef Heuger
Filed: Concurrently with the instant application (U.S. Plant patent application Ser. No. 16/873,636)
Title: *Helleborus* Plant Named 'COSEH 8100'
Inventor/Applicant: Josef Heuger
Filed: Concurrently with the instant application (U.S. Plant patent application Ser. No. 16/873,649)

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 6, 2019, application number 2019/1391. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus niger* X *Helleborus* x *hybridus* and hereinafter referred to by the name 'COSEH 7400'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2011 of a proprietary selection of *Helleborus niger* identified as code number P780, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in December, 2013.

Asexual reproduction of the new *Helleborus* plant by in vitro axillary meristem culture in a controlled environment in Glandorf, Germany since March, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 7400'. These characteristics in combination distinguish 'COSEH 7400' as a new and distinct *Helleborus* plant:

1. Upright to slightly outwardly spreading and mounded plant habit.
2. Moderately vigorous growth habit.
3. Dark green-colored leaves.

4. Moderately freely flowering habit.
5. Large light yellow green to white-colored flowers with red purple-colored margins and reverse.
6. Good garden performance.

Plants of the new *Helleborus* differ from plants of the female parent selection in the following characteristics:

1. Plants of the new *Helleborus* are more vigorous than plants of the female parent selection.
2. Flowers of plants of the new *Helleborus* are light yellow green to white in color whereas flowers of plants of the female parent selection are white in color.

Plants of the new *Helleborus* differ from plants of the male parent selection in the following characteristics:

1. Plants of the new *Helleborus* are more vigorous than plants of the male parent selection.
2. Flowers of plants of the new *Helleborus* are light yellow green to white in color whereas flowers of plants of the male parent selection are pinkish in color.

Plants of the new *Helleborus* can be compared to plants of *Helleborus niger* X *Helleborus* x *hybridus* 'COSEH 7300', disclosed in a U.S. Plant Patent application filed concurrently. Plants of the new *Helleborus* differ primarily from plants of 'COSEH 7300' in flower color as plants of new *Helleborus* are light yellow green to white in color whereas flowers of plants of 'COSEH 7300' are dark greyed purple in color.

Plants of the new *Helleborus* can be compared to plants of *Helleborus niger* X *Helleborus* x *hybridus* 'COSEH 8100', disclosed in a U.S. Plant Patent application filed concurrently. Plants of the new *Helleborus* differ primarily from plants of 'COSEH 8100' in flower color as flowers of plants of the new *Helleborus* are light yellow green to white in color whereas flowers of plants of 'COSEH 8100' are red purple to greyed purple in color. In addition, plants of the new *Helleborus* have larger flowers than plants of 'COSEH 8100'.

Plants of the new *Helleborus* can also be compared to plants of *Helleborus niger* X *Helleborus* x *hybridus* 'ABCRD02', disclosed in U.S. Plant Pat. No. 24,720. In side-by-side comparisons, plants of the new *Helleborus* differ primarily from plants of 'ABCRD02' in the following characteristics:

1. Plants of the new *Helleborus* differ are more vigorous than plants of 'ABCRD02'.
2. Plants of the new *Helleborus* and 'ABCRD02' differ in flower color as plants of the new *Helleborus* have light yellow green to white-colored flowers whereas plants of 'ABCRD02' have purple-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 7400' grown in a container.

Figure 2:
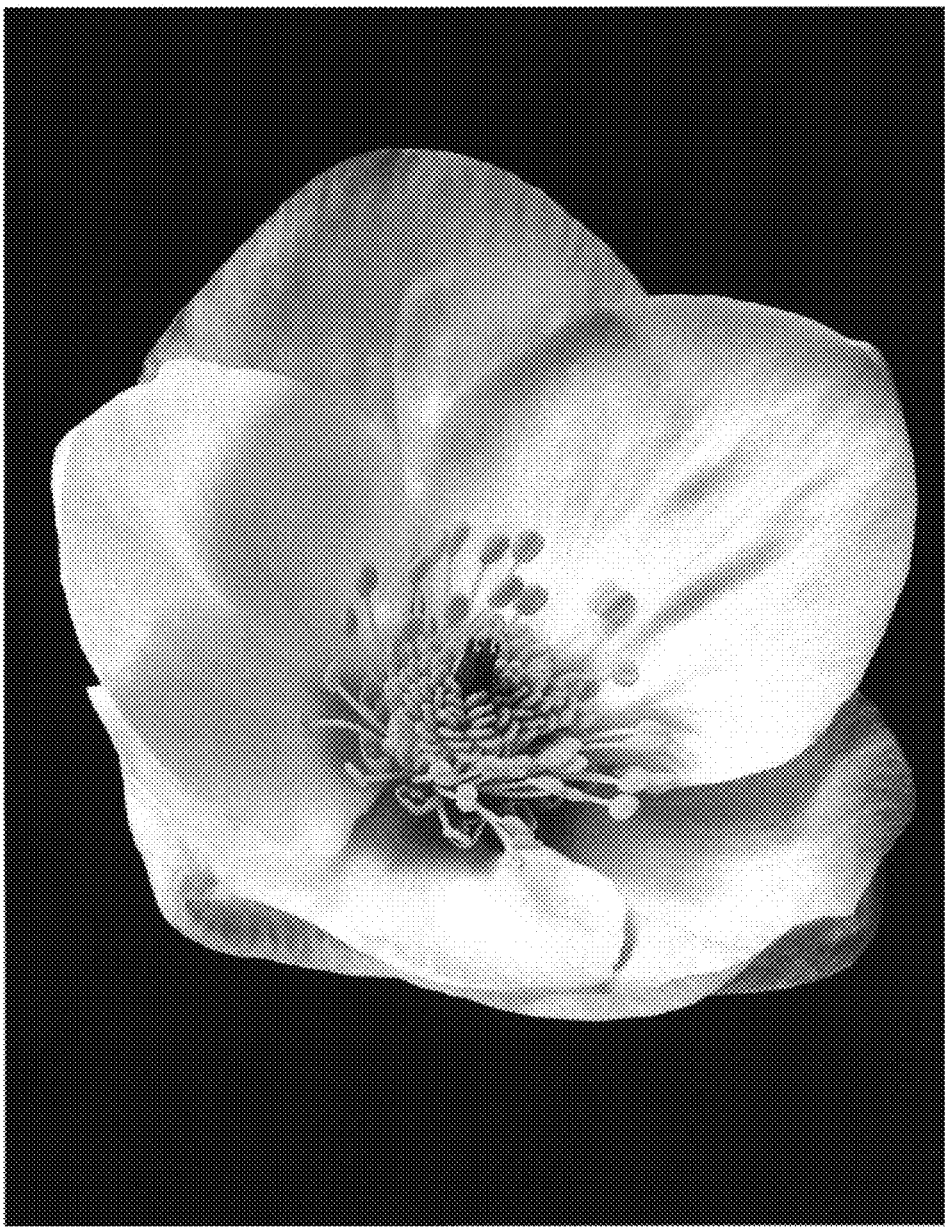

The photograph on the second sheet (FIG. 2 of 2) is a close-up view of a typical flower of 'COSEH 7400'.

DETAILED BOTANICAL DESCRIPTION

The aforementioned photographs and following observations, measurements and values describe plants grown during March in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'COSEH 7400'.

Parentage:

*Female, or seed, parent*.—Proprietary selection of *Helleborus niger* disclosed as code number P780, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to slightly outwardly spreading and mounding plant habit with flowers held within and above the foliar plane; plant shape, broadly ovate; moderately vigorous growth habit and moderate growth rate.

*Plant height, soil level to top of foliar plane*.—About 23.3 cm.

*Plant height, soil level to top of flowers*.—About 48.6 cm.

*Plant diameter* (*area of spread*).—About 40.1 cm.

Leaf description:

*Arrangement*.—Leaves arranged in a basal rosette; leaves palmately compound with typically five leaflets per leaf.

*Leaf length*.—About 17.5 cm.

*Leaf width*.—About 17.5 cm.

*Leaflet length*.—About 10 cm.

*Leaflet width*.—About 6.1 cm.

*Leaf shape*.—Palmate; orbicular to reniform in outline.

*Leaflet shape*.—Obovate to broadly elliptic; lower leaflets occasionally cleft.

*Leaflet apex*.—Acute.

*Leaflet base*.—Attenuate.

*Leaflet margin*.—Coarsely serrate; slightly and coarsely undulate.

*Leaflet texture and luster, upper and lower surfaces*.—Smooth, glabrous; leathery; slightly glossy.

*Leaflet venation pattern*.—Pinnate.

*Leaflet color*.—Developing leaflets, upper surface: Close to NN137C; midvein tinged at the base with close to N186C. Developing leaflets, lower surface: Close to 146B; midvein tinged at the base with close to 183A. Fully developed leaflets, upper surface: Darker than between NN137A and 147A; venation, close to 144A. Fully developed leaflets, lower surface: Close to 147B; venation, close to 147D.

*Petioles*.—Length: About 9.9 cm. Diameter: About 5.5 mm to 6 mm. Strength: Strong. Texture and luster, upper and lower surfaces: Smooth, glabrous; moderately glossy. Color, upper surface: Close to between 144A and 144B; proximally, close to N199B. Color, lower surface: Close to between 144A and 144B; proximally, close to between N199B and 200B.

Flower description:

*Flower shape and habit*.—Rotate flowers; flowers slightly cupped; arranged in panicles; moderately freely flowering habit with about two flowers per inflorescence and about 26 flowers developing per plant; flowers face mostly outwardly to slightly nodding.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 2.2 cm. Diameter: About 1.2 cm. Shape: Ovate. Texture and luster: Smooth, glabrous; matte. Color: Close to NN155A to NN155D; towards the base, close to 146C; venation, close to 68B.

*Inflorescence height* (*including peduncle*).—About 41.1 cm.

*Inflorescence diameter*.—About 11.7 cm.

*Flower diameter*.—About 10 cm by 10 cm.

*Flower depth* (*height*).—About 2.9 cm.

*Petals*.—All petals are transformed into nectaries.

*Sepals*.—Quantity and arrangement: About five, arranged in a single whorl. Length: About 5 cm. Width: About 4.2 cm. Shape: Broadly ovate, slightly concave. Apex: Obtuse. Base: Broadly cuneate. Margin: Entire; moderately undulate. Texture and luster, upper surface: Smooth, glabrous; matte. Texture and luster, lower surface: Smooth, glabrous; matte to slightly glossy. Color: When opening, upper surface: Close to NN155C; towards the base, close to 144B; venation, close to 70C. When opening, lower surface: Close to NN155B to NN155C; towards the margins and apex, slightly tinged with close to 70D; towards the base, close to 146B to 146C; venation, close to 70C. Fully opened, upper surface: Close to between 145B and 145C; towards the base, close to 144B; towards the margins, close to 157D and tinged with close to 70D; venation, close to 145A to 145B; with development, becoming closer to between 144B and 146C. Fully opened, lower surface: Close to 145C; towards the base, close to 146C; towards the margins, close to between 145D and 157C tinged with close to 70D; venation, close to 199C; with development, becoming closer to between 144B and 146A to 146C and 70D, towards the base, close to 181A and venation, between 197B and 199B.

*Flower bracts*.—Quantity per flower: Typically one or two. Length: About 5 cm. Width: About 3.8 cm. Shape: Ovate to tri-lobed. Apex: Acute. Base: Truncate. Margin: Mostly entire and distally, finely serrate. Color, upper surface: Close to NN137A; venation, similar to lamina. Color, lower surface: Close to 147B; midvein, tinged with close to 178A.

*Peduncles*.—Length: About 25.7 cm. Diameter: About 8 mm. Aspect: About 12.5° from vertical. Strength: Strong. Texture and luster: Smooth, glabrous; moderately glossy. Color: Close to 144C, moderately to heavily covered with fine dots and stripes, close to 177D.

*Pedicels*.—Length: About 1.8 cm. Diameter: About 2.5 mm. Aspect: About 10° to 20° from peduncle axis. Strength: Moderately strong. Texture and luster: Smooth, glabrous; slightly glossy. Color: Close to 148B covered with fine dots, close to 177D.

*Reproductive organs*.—Stamens: Quantity per flower: About 70. Filament length: About 1.7 cm. Filament color: Close to 157C. Anther shape: Double and broadly reniform; basifixed. Anther size: About 2 mm by 3 mm. Anther color: Close to between 150C and 151D. Pollen amount: Sparse to moderate. Pollen color: Lighter than 4D. Pistils: Quantity per flower: About six to nine. Pistil length: About 1.2 cm. Stigma diameter: About 0.3 mm. Stigma shape: Club-shaped. Stigma color: Close to 145D. Style length: About 1.1 cm. Style color: Close to 181C. Ovary color: Close to 144B. Nectaries (transformed petals): Quantity per flower: About 13. Length: About 1.4 cm. Diameter: About 3 mm. Shape: Tubular, flattened. Texture and luster, inner and outer surfaces: Smooth, glabrous; slightly glossy. Color, immature, inner and outer surfaces: Close to 144B; towards the apex, close to 144C. Color, mature, inner and outer surfaces: Close to 144A; towards the apex, close to 151D; venation, similar to lamina; color does not change with development.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 7400' as illustrated and described.

* * * * *